US012801834B2

(12) United States Patent
Nakamura et al.

(10) Patent No.: US 12,801,834 B2
(45) Date of Patent: Nov. 17, 2026

(54) DOCUMENT CREATION SUPPORT APPARATUS, DOCUMENT CREATION SUPPORT METHOD, AND DOCUMENT CREATION SUPPORT PROGRAM

(71) Applicant: FUJIFILM Corporation, Tokyo (JP)

(72) Inventors: Keigo Nakamura, Tokyo (JP); Noriaki Ida, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 226 days.

(21) Appl. No.: 18/489,850

(22) Filed: Oct. 19, 2023

(65) Prior Publication Data

US 2024/0046028 A1 Feb. 8, 2024

Related U.S. Application Data

(63) Continuation of application No. PCT/JP2022/017410, filed on Apr. 8, 2022.

(30) Foreign Application Priority Data

Apr. 30, 2021 (JP) ................................. 2021-077650
Dec. 22, 2021 (JP) ................................. 2021-208521

(51) Int. Cl.

| | |
|---|---|
| ***G06V 10/25*** | (2022.01) |
| ***G06F 40/166*** | (2020.01) |
| ***G16H 15/00*** | (2018.01) |
| ***G16H 30/40*** | (2018.01) |

(52) U.S. Cl.

CPC ............ *G06F 40/166* (2020.01); *G06V 10/25* (2022.01); *G16H 15/00* (2018.01); *G16H 30/40* (2018.01)

(58) Field of Classification Search

CPC .................................................... G06T 7/0012
See application file for complete search history.

(56) References Cited

U.S. PATENT DOCUMENTS

| | | | | |
|---|---|---|---|---|
| 9,117,009 | B2 | 8/2015 | Iizuka et al. | |
| 10,521,909 | B2 | 12/2019 | Kikuchi | |
| 11,238,976 | B2 * | 2/2022 | Fuchigami | A61B 6/48 |

(Continued)

FOREIGN PATENT DOCUMENTS

| | | | | |
|---|---|---|---|---|
| CN | 110322436 B | * 10/2020 | | G06F 18/24 |
| CN | 114730488 A | * 7/2022 | | G06V 10/30 |

(Continued)

OTHER PUBLICATIONS

"International Search Report (Form PCT/ISA/210) of PCT/JP2022/017410", mailed on Jul. 12, 2022, with English translation thereof, pp. 1-5.

(Continued)

*Primary Examiner* — Di Xiao
(74) *Attorney, Agent, or Firm* — JCIPRNET

(57) ABSTRACT

A document creation support apparatus acquires a medical image and information indicating a plurality of regions of interest included in the medical image, generates a plurality of comments on findings for two or more regions of interest among the plurality of regions of interest, performs control to display the plurality of comments on findings, receives selection of one comment on findings from among the plurality of comments on findings, and generates a medical document including the one comment on findings.

19 Claims, 10 Drawing Sheets

(56) References Cited

U.S. PATENT DOCUMENTS

| | | | |
|---|---|---|---|
| 11,984,207 B2 | 5/2024 | Hasegawa | |
| 2005/0114283 A1 | 5/2005 | Pearson et al. | |
| 2009/0087049 A1 | 4/2009 | Takahashi | |
| 2014/0286561 A1* | 9/2014 | Remiszewski | G06V 30/1916 382/133 |
| 2014/0292814 A1 | 10/2014 | Tsujimoto et al. | |
| 2015/0262014 A1 | 9/2015 | Iwamura et al. | |
| 2017/0091949 A1 | 3/2017 | Akasaka et al. | |
| 2017/0337329 A1 | 11/2017 | Liu et al. | |
| 2020/0110914 A1* | 4/2020 | Mackay | G06F 16/168 |
| 2020/0160982 A1* | 5/2020 | Gurson | G06N 3/0464 |
| 2021/0312625 A1* | 10/2021 | Gutmann | A61B 17/66 |
| 2022/0076796 A1 | 3/2022 | Momoki | |

FOREIGN PATENT DOCUMENTS

| | | | |
|---|---|---|---|
| JP | H0785029 | 3/1995 | |
| JP | H07323024 | 12/1995 | |
| JP | 2009086765 | 4/2009 | |
| JP | 2012118583 | 6/2012 | |
| JP | 2013152699 | 8/2013 | |
| JP | 2015187845 | 10/2015 | |
| JP | 2017068380 | 4/2017 | |
| JP | 2017189390 | 10/2017 | |
| WO | 2020202822 | 10/2020 | |
| WO | 2020241857 | 12/2020 | |
| WO | WO-2020264029 A1 * | 12/2020 | G06V 10/34 |
| WO | WO-2021029625 A1 * | 2/2021 | G01N 23/18 |
| WO | WO-2021084352 A1 * | 5/2021 | A61B 5/7275 |

OTHER PUBLICATIONS

"Written Opinion of the International Searching Authority (Form PCT/ISA/237) of PCT/JP2022/017410", mailed on Jul. 12, 2022, with English translation thereof, pp. 1-8.

"Notice of Reasons for Refusal of Japan Counterpart Application", issued on Jul. 21, 2026, with English translation thereof, p. 1-p. 5.

"Notice of Reasons for Refusal of Japan Counterpart Application", issued on Mar. 3, 2026, with English translation thereof, p. 1-p. 6.

* cited by examiner

GROUP 1: (A) THREE TUMORS ARE FOUND IN RIGHT LUNG.
(B) TWO TUMORS IN RIGHT LUNG AND ONE BRONCHIAL HYPERTROPHY ASSOCIATED WITH TUMORS ARE FOUND. (C) ⋯
GROUP 2: (A) TWO LYMPHOMAS ARE FOUND IN LEFT LUNG. (B) ⋯
GROUP 3: (A) ONE SITE OF OSTEOLYSIS IS FOUND. (B) ⋯
GROUP 4: ⋯

DOCUMENT CREATION SUPPORT APPARATUS, DOCUMENT CREATION SUPPORT METHOD, AND DOCUMENT CREATION SUPPORT PROGRAM

CROSS-REFERENCE TO RELATED APPLICATIONS

This application is a continuation of International Application No. PCT/JP2022/017410, filed on Apr. 8, 2022, which claims priority from Japanese Patent Application No. 2021-077650, filed on Apr. 30, 2021 and Japanese Patent Application No. 2021-208521, filed on Dec. 22, 2021. The entire disclosure of each of the above applications is incorporated herein by reference.

BACKGROUND

1. Technical Field

The present disclosure relates to a document creation support apparatus, a document creation support method, and a document creation support program.

2. Description of the Related Art

In the related art, there have been proposed technologies for improving the efficiency of creation of a medical document such as an interpretation report by a doctor. For example, JP1995-323024A (JP-H7-323024A) discloses a technology of obtaining a part indicated by coordinates on a medical image designated by a doctor from the designated coordinates and data obtained by dividing the medical image into regions for each part, and outputting the part with an abnormality and a name of a disease.

Further, JP2017-068380A discloses a technology of displaying an individual input region for inputting individual findings information for each of a plurality of regions of interest in a medical image and a common input region for inputting findings information common to the regions of interest included in the same group.

SUMMARY

However, in the technology disclosed in JP1995-323024A (JP-H7-323024A), since disease names are individually output for each of a plurality of regions of interest, in a case of creating a medical document for the entire medical image including the plurality of regions of interest, which may increase a burden on a doctor. In addition, in the technology disclosed in JP2017-068380A, only an input region for findings information is presented and a doctor inputs the findings information, which may increase a burden on the doctor. In these cases, the creation of medical documents cannot be appropriately supported.

The present disclosure has been made in view of the above circumstances, and an object of the present disclosure is to provide a document creation support apparatus, a document creation support method, and a document creation support program capable of appropriately supporting the creation of a medical document even in a case where a medical image includes a plurality of regions of interest.

According to an aspect of the present disclosure, there is provided a document creation support apparatus comprising at least one processor, in which the processor is configured to: acquire a medical image and information indicating a plurality of regions of interest included in the medical image; generate a plurality of comments on findings for two or more regions of interest among the plurality of regions of interest; perform control to display the plurality of comments on findings; receive selection of one comment on findings from among the plurality of comments on findings; and generate a medical document including the one comment on findings.

In addition, in the document creation support apparatus according to the aspect of the present disclosure, the processor may be configured to: classify the plurality of regions of interest into at least one group through an analysis process on the medical image; and generate a plurality of comments on findings for two or more regions of interest included in the same group.

In addition, in the document creation support apparatus according to the aspect of the present disclosure, the processor may be configured to classify two or more regions of interest into the same group based on a degree of similarity of an image of a region-of-interest portion included in the medical image.

In addition, in the document creation support apparatus according to the aspect of the present disclosure, the processor may be configured to classify two or more regions of interest into the same group based on a degree of similarity of a feature amount extracted from an image of a region-of-interest portion included in the medical image.

In addition, in the document creation support apparatus according to the aspect of the present disclosure, the processor may be configured to classify two or more regions of interest having the same disease name derived from the region of interest into the same group.

In addition, in the document creation support apparatus according to the aspect of the present disclosure, the processor may be configured to: generate a comment on findings for each of the plurality of regions of interest; and classify two or more regions of interest into the same group based on a degree of similarity of the generated comment on findings.

In addition, in the document creation support apparatus according to the aspect of the present disclosure, the processor may be configured to classify two or more regions of interest of which a distance between the regions of interest is less than a threshold value into the same group.

In addition, in the document creation support apparatus according to the aspect of the present disclosure, the processor may be configured to classify the plurality of regions of interest into at least one group based on anatomical relevance of the regions of interest.

In addition, in the document creation support apparatus according to the aspect of the present disclosure, the processor may be configured to classify the plurality of regions of interest into at least one group based on relevance of disease features of the regions of interest.

In addition, in the document creation support apparatus according to the aspect of the present disclosure, the processor may be configured to: perform control to display the medical image after generating the plurality of comments on findings; receive designation of a region of interest on the medical image; and perform control to display the plurality of comments on findings for two or more regions of interest in the same group as the designated region of interest.

In addition, in the document creation support apparatus according to the aspect of the present disclosure, the processor may be configured to, in a case where designation of at least one region of interest in a group is received, perform control to display the plurality of comments on findings for two or more regions of interest of the group.

In addition, in the document creation support apparatus according to the aspect of the present disclosure, the processor may be configured to, in a case where designation of a majority of regions of interest in the group is received, perform control to display the plurality of comments on findings for two or more regions of interest of the group.

In addition, in the document creation support apparatus according to the aspect of the present disclosure, the processor may be configured to, in a case where designation of all regions of interest in the group is received, perform control to display the plurality of comments on findings for two or more regions of interest of the group.

In addition, in the document creation support apparatus according to the aspect of the present disclosure, the processor may be configured to, in a case where the designation of the region of interest on the medical image is received and then an instruction to generate a comment on findings is received, perform control to display the plurality of comments on findings for the two or more regions of interest in the same group as the designated region of interest.

In addition, in the document creation support apparatus according to the aspect of the present disclosure, the processor may be configured to, in a case where the instruction to generate the comment on findings is received and there is an undesignated region of interest in the regions of interest in the same group as the designated region of interest, notify that there is an undesignated region of interest.

In addition, in the document creation support apparatus according to the aspect of the present disclosure, the processor may be configured to, in a case where the instruction to generate the comment on findings is received and there is an undesignated region of interest in the regions of interest in the same group as the designated region of interest, perform control to display information indicating the undesignated region of interest.

In addition, in the document creation support apparatus according to the aspect of the present disclosure, the processor may be configured to, in a case where the instruction to generate the comment on findings is received and two or more designated regions of interest belong to a plurality of different groups, generate a plurality of comments on findings for the two or more designated regions of interest.

In addition, in the document creation support apparatus according to the aspect of the present disclosure, the processor may be configured to: classify two or more regions of interest into one group based on an input from a user; and generate a plurality of comments on findings only for the two or more regions of interest included in the one group among the plurality of regions of interest.

In addition, in the document creation support apparatus according to the aspect of the present disclosure, the processor may be configured to classify two or more regions of interest included in a region designated by the user in the medical image into one group.

In addition, in the document creation support apparatus according to the aspect of the present disclosure, the processor may be configured to classify two or more regions of interest individually designated by the user into one group.

In addition, in the document creation support apparatus according to the aspect of the present disclosure, the processor may be configured to: classify the plurality of regions of interest into at least one group through an analysis process on the medical image; and in a case where designation of a region of interest on the medical image is received and there is an undesignated region of interest in the regions of interest in the same group as the designated region of interest, perform control to display information recommending designation of the undesignated region of interest.

In addition, in the document creation support apparatus according to the aspect of the present disclosure, the processor may be configured to classify the plurality of regions of interest into at least one group through an analysis process on the medical image; and in a case where designation of a region of interest on the medical image is received and there is an undesignated region of interest in the regions of interest in the same group as the designated region of interest, classify the undesignated region of interest into the same group as the region of interest designated by the user.

In addition, according to another aspect of the present disclosure, there is provided a document creation support method executed by a processor provided in a document creation support apparatus, the method comprising: acquiring a medical image and information indicating a plurality of regions of interest included in the medical image; generating a plurality of comments on findings for two or more regions of interest among the plurality of regions of interest; performing control to display the plurality of comments on findings; receiving selection of one comment on findings from among the plurality of comments on findings; and generating a medical document including the one comment on findings.

In addition, according to another aspect of the present disclosure, there is provided a document creation support program for causing a processor provided in a document creation support apparatus to execute: acquiring a medical image and information indicating a plurality of regions of interest included in the medical image; generating a plurality of comments on findings for two or more regions of interest among the plurality of regions of interest; performing control to display the plurality of comments on findings; receiving selection of one comment on findings from among the plurality of comments on findings; and generating a medical document including the one comment on findings.

According to the aspects of the present disclosure, it is possible to appropriately support the creation of a medical document even in a case where a medical image includes a plurality of regions of interest.

DETAILED DESCRIPTION

Hereinafter, form examples for implementing a technology of the present disclosure will be described in detail with reference to the drawings.

First Embodiment

First, a configuration of a medical information system 1 to which a document creation support apparatus according to the disclosed technology is applied will be described with reference to FIG. 1. The medical information system 1 is a system for performing imaging of a diagnosis target part of a subject and storing of a medical image acquired by the imaging based on an examination order from a doctor in a medical department using a known ordering system. In addition, the medical information system 1 is a system for performing interpretation of a medical image and creation of an interpretation report by a radiologist, and viewing the interpretation report and detailed observation of the medical image to be interpreted by a doctor of a medical department that is a request source.

Figure 1:
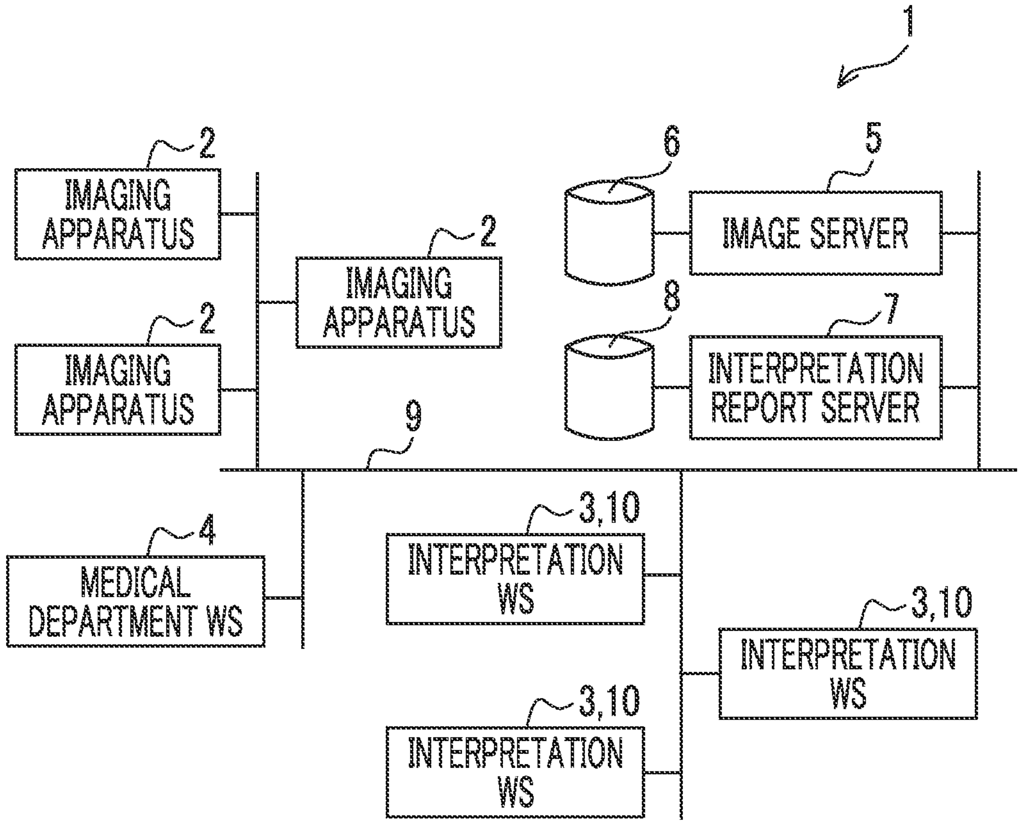
FIG. 1 is a block diagram showing a schematic configuration of a medical information system.

As shown in FIG. 1, the medical information system 1 according to the present embodiment includes a plurality of imaging apparatuses 2, a plurality of interpretation workstations (WS) 3 that are interpretation terminals, a medical department WS 4, an image server 5, an image database (DB) 6, an interpretation report server 7, and an interpretation report DB 8. The imaging apparatus 2, the interpretation WS 3, the medical department WS 4, the image server 5, and the interpretation report server 7 are connected to each other via a wired or wireless network 9 in a communicable state. In addition, the image DB 6 is connected to the image server 5, and the interpretation report DB 8 is connected to the interpretation report server 7.

The imaging apparatus 2 is an apparatus that generates a medical image showing a diagnosis target part of a subject by imaging the diagnosis target part. The imaging apparatus 2 may be, for example, a simple X-ray imaging apparatus, an endoscope apparatus, a computed tomography (CT) apparatus, a magnetic resonance imaging (MRI) apparatus, a positron emission tomography (PET) apparatus, and the like. A medical image generated by the imaging apparatus 2 is transmitted to the image server 5 and is saved therein.

The medical department WS 4 is a computer used by a doctor in the medical department for detailed observation of a medical image, viewing of an interpretation report, creation of an electronic medical record, and the like. In the medical department WS 4, each process such as creating an electronic medical record of a patient, requesting the image server 5 to view an image, and displaying a medical image received from the image server 5 is performed by executing a software program for each process. In addition, in the medical department WS 4, each process such as automatically detecting or highlighting suspected disease regions in the medical image, requesting to view an interpretation report from the interpretation report server 7, and displaying the interpretation report received from the interpretation report server 7 is performed by executing a software program for each process.

The image server 5 incorporates a software program that provides a function of a database management system (DBMS) to a general-purpose computer. In a case where the image server 5 receives a request to register a medical image from the imaging apparatus 2, the image server 5 prepares the medical image in a format for a database and registers the medical image in the image DB 6.

Image data representing the medical image acquired by the imaging apparatus 2 and accessory information attached to the image data are registered in the image DB 6. The accessory information includes information such as an image identification (ID) for identifying individual medical images, a patient ID for identifying a patient who is a subject, an examination ID for identifying examination content, and a unique identification (UID) assigned to each medical image, for example. In addition, the accessory information includes information such as an examination date when a medical image was generated, an examination time, the type of imaging apparatus used in the examination for acquiring the medical image, patient information (for example, a name, an age, and a gender of the patient), an examination part (that is, an imaging part), and imaging information (for example, an imaging protocol, an imaging sequence, an imaging method, imaging conditions, and whether or not a contrast medium is used), and a series number or collection number when a plurality of medical images are acquired in one examination. In addition, in a case where a viewing request from the interpretation WS 3 is received through the network 9, the image server 5 searches for a medical image registered in the image DB 6 and transmits the searched for medical image to the interpretation WS 3 that is a request source.

The interpretation report server 7 incorporates a software program for providing a function of DBMS to a general-purpose computer. In a case where the interpretation report server 7 receives a request to register an interpretation report from the interpretation WS 3, the interpretation report server 7 prepares the interpretation report in a format for a database and registers the interpretation report in the interpretation report database 8. Further, in a case where the request to search for the interpretation report is received, the interpretation report is searched for from the interpretation report DB 8.

In the interpretation report DB 8, for example, an interpretation report is registered in which information, such as an image ID for identifying a medical image to be interpreted, a radiologist ID for identifying an image diagnostician who performed the interpretation, a lesion name, position information of a lesion, findings, and a degree of certainty of the findings, is recorded.

The network 9 is a wired or wireless local area network that connects various apparatuses in a hospital to each other. In a case where the interpretation WS 3 is installed in another hospital or clinic, the network 9 may be configured to connect local area networks of respective hospitals through the Internet or a dedicated line. In any case, it is preferable that the network 9 has a configuration capable of realizing high-speed transmission of medical images such as an optical network.

The interpretation WS 3 requests the image server 5 to view a medical image, performs various types of image processing on the medical image received from the image server 5, displays the medical image, performs an analysis process on the medical image, highlights the medical image based on an analysis result, and creates an interpretation report based on the analysis result. In addition, the interpretation WS 3 supports creation of an interpretation report, requests the interpretation report server 7 to register and view an interpretation report, displays the interpretation report received from the interpretation report server 7, and the like. The interpretation WS 3 performs each of the above processes by executing a software program for each process. The interpretation WS 3 encompasses a document creation support apparatus 10, which will be described later, and in the above processes, processes other than those performed by the document creation support apparatus 10 are performed by a well-known software program, and therefore the detailed description thereof will be omitted here. In addition, processes other than the processes performed by the document creation support apparatus 10 may not be performed in the interpretation WS 3, and a computer that performs the processes may be separately connected to the network 9, and in response to a processing request from the interpretation WS 3, the requested process may be performed by the computer. Hereinafter, the document creation support apparatus 10 encompassed in the interpretation WS 3 will be described in detail.

Figure 2:
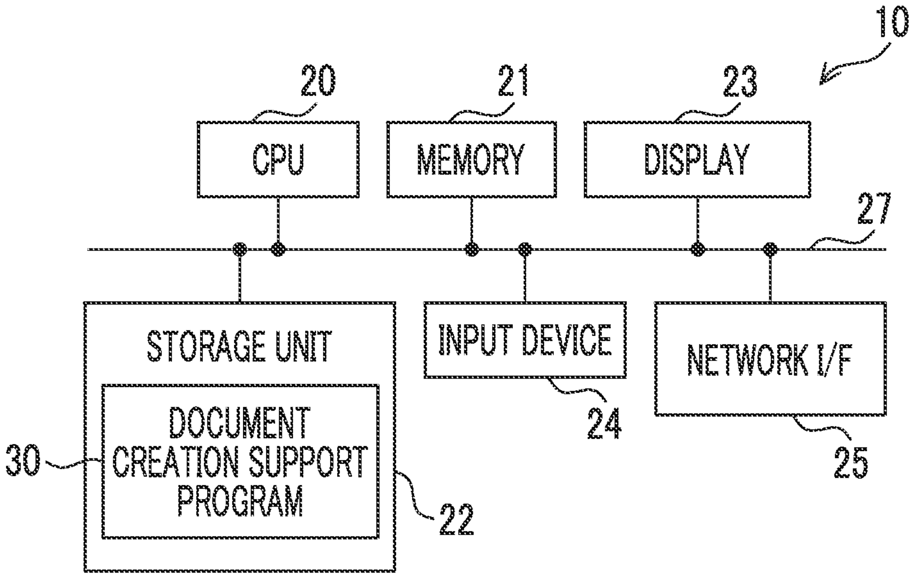
FIG. 2 is a block diagram showing an example of a hardware configuration of a document creation support apparatus.

Next, a hardware configuration of the document creation support apparatus 10 according to the present embodiment will be described with reference to FIG. 2. As shown in FIG. 2, the document creation support apparatus 10 includes a central processing unit (CPU) 20, a memory 21 as a temporary storage area, and a non-volatile storage unit 22. Further, the document creation support apparatus 10 includes a display 23 such as a liquid crystal display, an input device 24 such as a keyboard and a mouse, and a network interface (I/F) 25 connected to the network 9. The CPU 20, the memory 21, the storage unit 22, the display 23, the input device 24, and the network OF 25 are connected to a bus 27.

The storage unit 22 is realized by a hard disk drive (HDD), a solid state drive (SSD), a flash memory, or the like. A document creation support program 30 is stored in the storage unit 22 as a storage medium. The CPU 20 reads out the document creation support program 30 from the storage unit 22, loads the read document creation support program 30 into the memory 21, and executes the loaded document creation support program 30.

Figure 3:
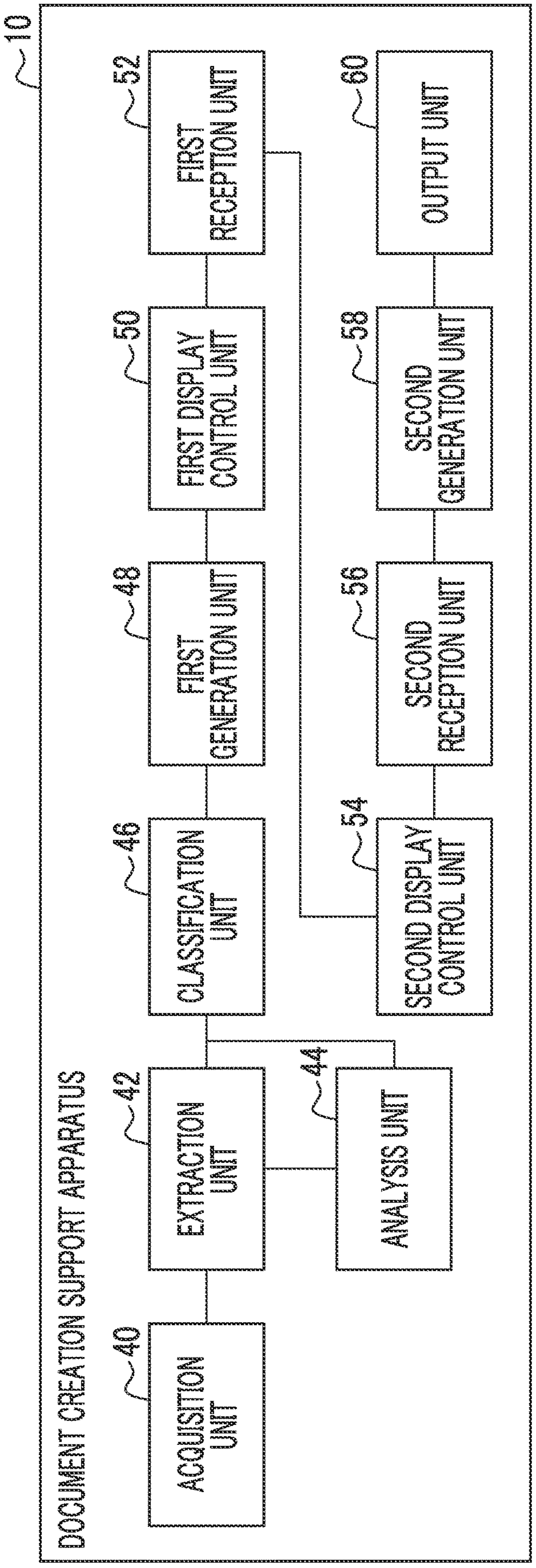
FIG. 3 is a block diagram showing an example of a functional configuration of a document creation support apparatus according to a first embodiment.

Next, a functional configuration of the document creation support apparatus 10 according to the present embodiment will be described with reference to FIG. 3. As shown in FIG. 3, the document creation support apparatus 10 includes an acquisition unit 40, an extraction unit 42, an analysis unit 44, a classification unit 46, a first generation unit 48, a first display control unit 50, a first reception unit 52, a second display control unit 54, a second reception unit 56, a second generation unit 58, and an output unit 60. The CPU 20 executes the document creation support program 30 to function as the acquisition unit 40, the extraction unit 42, the analysis unit 44, the classification unit 46, the first generation unit 48, the first display control unit 50, the first reception unit 52, the second display control unit 54, the second reception unit 56, the second generation unit 58, and the output unit 60.

The acquisition unit 40 acquires a medical image to be diagnosed (hereinafter referred to as a "diagnosis target image") from the image server 5 via the network OF 25. In the following, a case where the diagnosis target image is a chest CT image will be described as an example.

The extraction unit 42 extracts a region including an abnormal shadow as an example of the region of interest in the diagnosis target image acquired by the acquisition unit 40. Specifically, the extraction unit 42 extracts a region including an abnormal shadow using a trained model M1 for detecting the abnormal shadow from the diagnosis target image. The abnormal shadow refers to a shadow suspected of having a disease such as a nodule. The trained model M1 is configured by, for example, a convolutional neural network (CNN) that receives a medical image as an input and outputs information about an abnormal shadow included in the medical image. The trained model M1 is, for example, a model trained by machine learning using, as training data, a large number of combinations of a medical image including an abnormal shadow and information specifying a region in the medical image in which the abnormal shadow is present.

The extraction unit 42 inputs the diagnosis target image to the trained model M1. The trained model M1 outputs information specifying a region in which an abnormal shadow included in the input diagnosis target image is present. In addition, the extraction unit 42 may extract a region including an abnormal shadow by a known computer-aided diagnosis (CAD), or may extract a region designated by a user as a region including the abnormal shadow.

The analysis unit 44 analyzes each of the abnormal shadows extracted by the extraction unit 42, and derives findings of the abnormal shadows. Specifically, the extraction unit 42 derives the findings of the abnormal shadow using a trained model M2 for deriving the findings of the abnormal shadow. The trained model M2 is configured by, for example, a CNN that receives, for example, a medical image including an abnormal shadow and information specifying a region in the medical image in which the abnormal shadow is present as inputs, and outputs a finding of the abnormal shadow. The trained model M2 is, for example, a model trained by machine learning using, as training data, a large number of combinations of a medical image including an abnormal shadow, information specifying a region in the medical image in which the abnormal shadow is present, and a finding of the abnormal shadow.

The analysis unit 44 inputs, to the trained model M2, information specifying a diagnosis target image and a region in which the abnormal shadow extracted by the extraction unit 42 for the diagnosis target image is present. The trained model M2 outputs findings of the abnormal shadow included in the input diagnosis target image. Examples of findings of the abnormal shadow include the position, size, transmittance (for example, solid or frosted glass), the presence or absence of a spicula, the presence or absence of calcification, the presence or absence of an irregular margin, the presence or absence of pleural invagination, the presence or absence of chest wall contact, the disease name of the abnormal shadow, and the like.

The classification unit 46 acquires information indicating a plurality of abnormal shadows included in the diagnosis target image from the extraction unit 42 and the analysis unit 44. The information indicating the abnormal shadow is, for example, information specifying a region in which the abnormal shadow extracted by the extraction unit 42 is present, and information including findings of the abnormal shadow derived by the analysis unit 44 for the abnormal shadow. In addition, the classification unit 46 may acquire information indicating a plurality of abnormal shadows included in the diagnosis target image from an external device such as the medical department WS 4. In this case, the extraction unit 42 and the analysis unit 44 are provided by the external device.

The classification unit 46 classifies a plurality of abnormal shadows extracted by the extraction unit 42 into at least one group based on the analysis result obtained by the analysis process of the diagnosis target image by the analysis unit 44.

In the present embodiment, the classification unit 46 classifies a plurality of abnormal shadows into at least one group based on anatomical relevance of the abnormal shadows. Specifically, the classification unit 46 classifies abnormal shadows located in the same region, which are anatomically divided regions, into the same group. The anatomically divided region may be a region of an organ such as a lung, may be regions such as a right lung and a left lung, or may be regions such as a right lung upper lobe, a right lung middle lobe, a right lung lower lobe, a left lung upper lobe, and a left lung lower lobe.

Figures 4, 5:
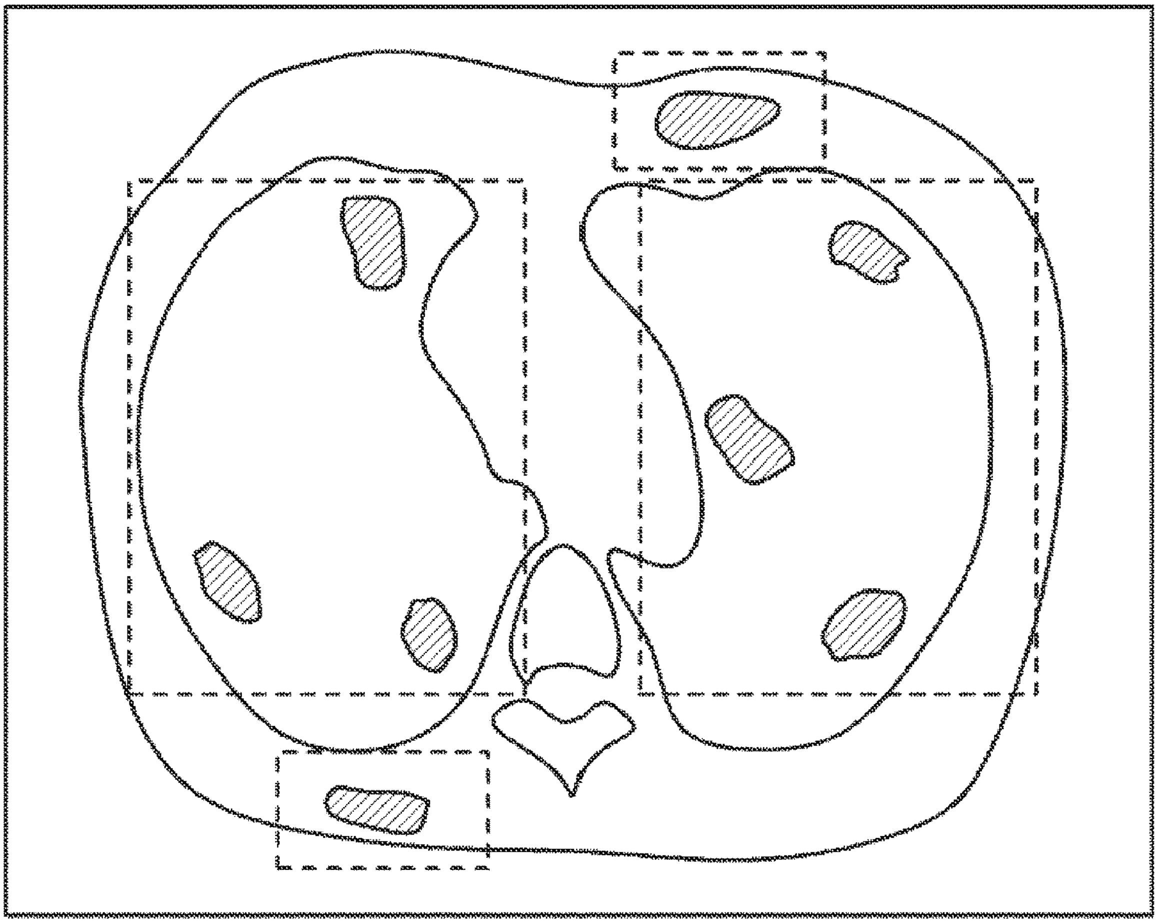
FIG. 4 is a diagram showing an example of a classification result of abnormal shadows.
FIG. 5 is a diagram showing an example of a plurality of comments on findings.

FIG. 4 shows an example of a classification result of abnormal shadows by the classification unit 46. In the example of FIG. 4, eight regions filled with diagonal lines indicate abnormal shadows. Further, the example of FIG. 4 shows that the abnormal shadows surrounded by the same broken-line rectangle are classified into the same group. That is, in the example of FIG. 4, eight abnormal shadows are classified into four groups.

Note that the classification unit 46 may classify two or more abnormal shadows whose degree of similarity of the image of the abnormal shadow portion included in the diagnosis target image is equal to or greater than a threshold value into the same group. As the degree of similarity of the images in this case, for example, a reciprocal of a distance of a feature amount vector obtained by vectorizing a plurality of feature amounts extracted from the image can be applied.

Further, the classification unit 46 may classify two or more abnormal shadows whose degree of similarity of a feature amount extracted from the image of the abnormal shadow portion included in the diagnosis target image is equal to or greater than a threshold value into the same group.

In addition, the classification unit 46 may classify two or more abnormal shadows having the same disease name derived by the analysis unit 44 for the abnormal shadows into the same group.

Further, the classification unit 46 may generate comments on findings for each of the plurality of abnormal shadows extracted by the extraction unit 42 based on the findings derived by the analysis unit 44, and may classify two or more abnormal shadows whose degree of similarity of the generated comments on findings is equal to or greater than a threshold value into the same group. For example, the classification unit 46 generates the comment on findings by inputting the findings derived by the analysis unit 44 to a recurrent neural network trained to generate text from input words. As the process of deriving the degree of similarity of the comments on findings, known methods such as a method of deriving the degree of similarity between sets by regarding words included in text as elements of a set and a method of deriving the degree of similarity in text using a neural network can be applied.

Further, the classification unit 46 may classify two or more abnormal shadows of which a distance between the abnormal shadows is less than a threshold value into the same group. As the distance between the abnormal shadows, for example, the distance between the centroids of the abnormal shadows can be applied.

Further, the classification unit 46 may classify a plurality of abnormal shadows into at least one group based on relevance of disease features of the abnormal shadows. Examples of the relevance of the disease features in this case include whether the cancer is primary or metastatic. In this case, for example, the classification unit 46 classifies a primary cancer and a metastatic cancer that has metastasized from the cancer into the same group.

The first generation unit 48 generates a plurality of comments on findings on two or more abnormal shadows included in the same group, for each group in which the abnormal shadows are classified by the classification unit 46. Specifically, the first generation unit 48 generates a plurality of comments on findings by inputting the findings derived by the analysis unit 44 for two or more abnormal shadows included in the same group to a recurrent neural network trained to generate text from input words. FIG. 5 shows an example of comments on findings generated for each group by the first generation unit 48. FIG. 5 shows an example in which a plurality of comments on findings regarding the abnormal shadow included in the group are generated for each of four groups.

The number of comments on findings may be two, may be three or more, or may be different between groups. Further, for example, in a case where a plurality of different sets of findings are derived by the analysis unit 44 together with a degree of certainty, the first generation unit 48 may generate a plurality of comments on findings having different findings. For example, in a case where a set of findings is derived by the analysis unit 44, the first generation unit 48 may generate a plurality of comments on findings having a different number of items of the findings included in the comments on findings. In addition, for example, the first generation unit 48 may generate a plurality of comments on findings having the same meaning but different expressions.

The first display control unit 50 performs control to display the diagnosis target image on the display 23 after the plurality of comments on findings are generated by the first generation unit 48. At the time of this control, the first display control unit 50 may perform control to highlight the abnormal shadow extracted by the extraction unit 42. In this case, for example, the first display control unit 50 performs control to highlight the abnormal shadow by filling a region of the abnormal shadow with a color set in advance, surrounding the abnormal shadow with a rectangular frame line, or the like.

The user performs an operation of designating an abnormal shadow for which an interpretation report is to be created as an example of a medical document on the diagnosis target image displayed on the display 23. The first reception unit 52 receives designation of one abnormal shadow on the diagnosis target image by the user.

The second display control unit 54 performs control to display, on the display 23, a plurality of comments on findings generated by the first generation unit 48 for the abnormal shadows whose designation is received by the first reception unit 52, that is, for two or more abnormal shadows in the same group as one abnormal shadow designated by the user.

Figure 6:
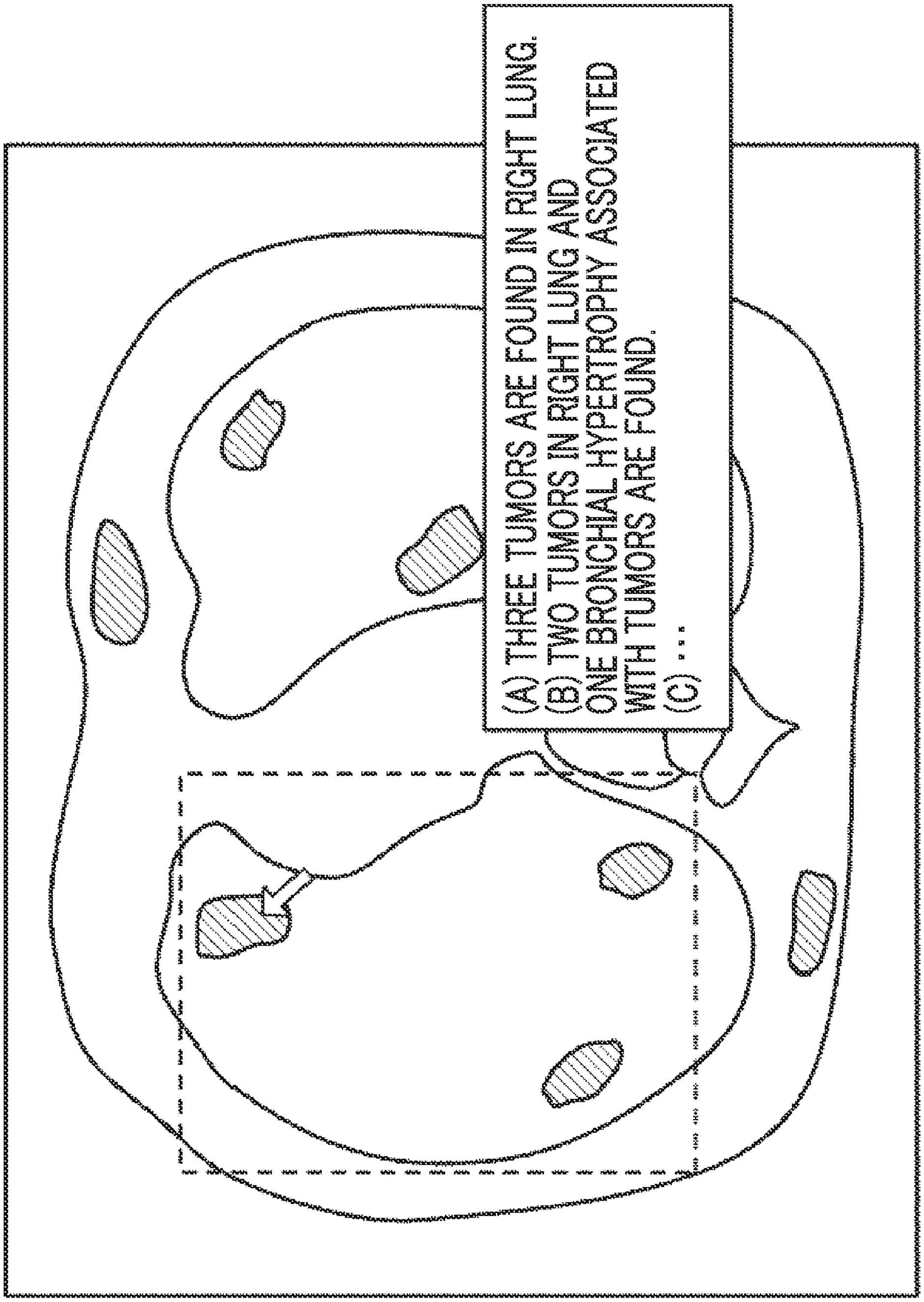
FIG. 6 is a diagram showing an example of a display screen for a plurality of comments on findings.

As shown in FIG. 6 as an example, a plurality of comments on findings for three abnormal shadows in the same group as the abnormal shadow designated by the user are displayed on the display 23 under the control of the second display control unit 54. In the example of FIG. 6, the abnormal shadow designated by the user is indicated by an arrow, and the abnormal shadow in the same group as the abnormal shadow is surrounded by a broken-line rectangle.

Figure 12:
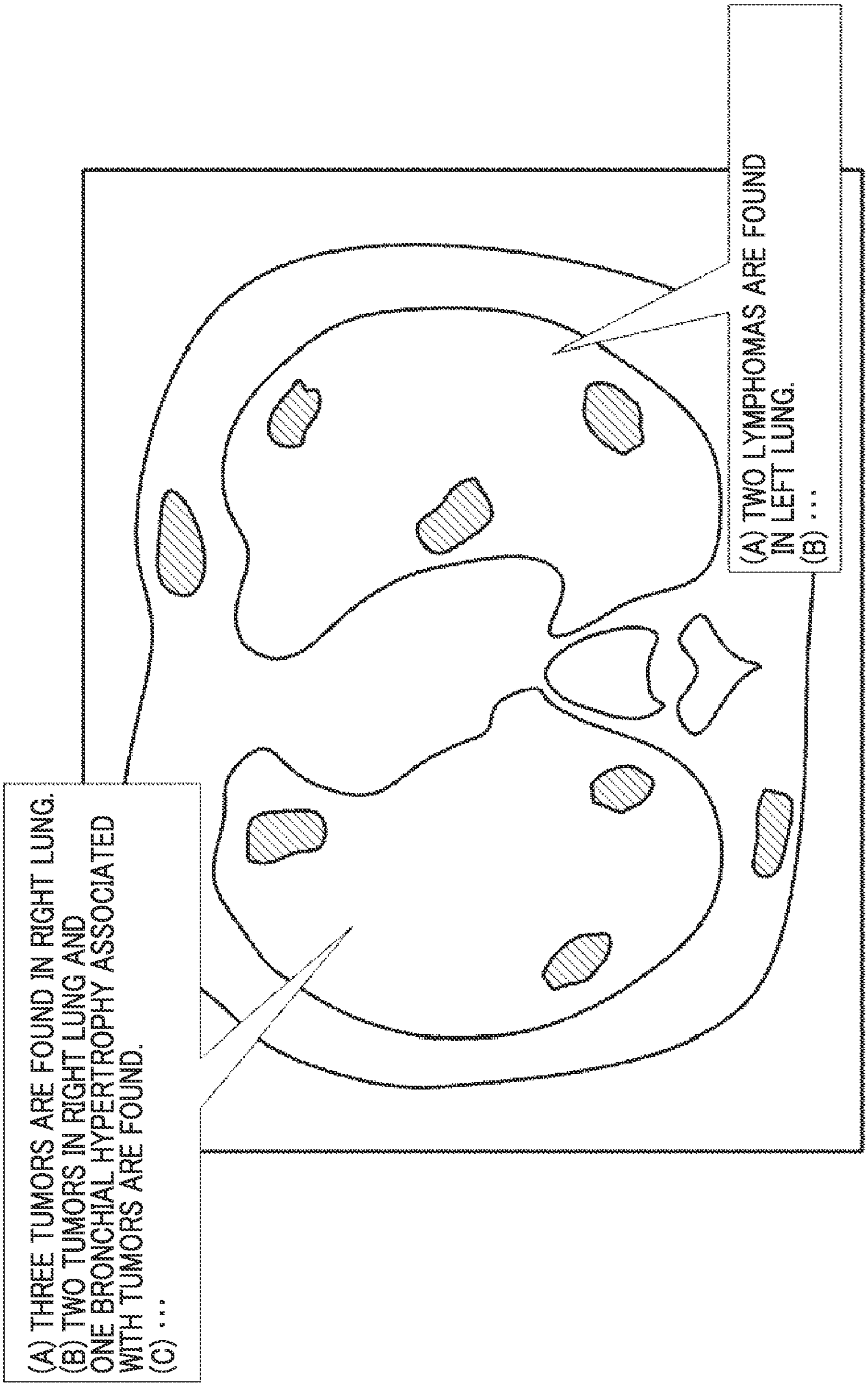
FIG. 12 is a diagram showing an example of a display screen for a plurality of comments on findings according to a modification example.

Note that the second display control unit 54 may perform control to display the plurality of comments on findings generated by the first generation unit 48 for each group. Specifically, as shown in FIG. 12 as an example, the second display control unit 54 performs control to display the plurality of comments on findings generated by the first generation unit 48 for each group at positions corresponding to each group. FIG. 12 shows an example in which a plurality of comments on findings of group 1 corresponding to the right lung are displayed at positions corresponding to the right lung, and a plurality of comments on findings of group 2 corresponding to the left lung are displayed at positions corresponding to the left lung.

Further, the second display control unit 54 may perform control to display the group in a visually recognizable manner. Specifically, for example, the second display control unit 54 performs control to display the broken line shown in FIG. 4 on the display 23.

Further, the second display control unit 54 may not display the comment on findings for a group to which an abnormal shadow located outside the predetermined region belongs. For example, in a case where the predetermined region is a lung region, the second display control unit 54 does not display the comment on findings for a group to which an abnormal shadow located outside the lung region belongs. In this case, only the comments on findings regarding group 1 and group 2 in the comments on findings shown in FIG. 5 are displayed on the display 23. Also, the predetermined region in this case may be set according to the purpose of diagnosis. For example, in a case where the user inputs that the purpose is diagnosis of a lung, the lung region is set as the predetermined region.

In addition, in a case where designation of two abnormal shadows in the group is received by the first reception unit 52, the second display control unit 54 may perform control to display, on the display 23, a plurality of comments on findings generated by the first generation unit 48 for two or more abnormal shadows in the group. In addition, in a case where designation of a majority of abnormal shadows in the group is received by the first reception unit 52, the second display control unit 54 may perform control to display, on the display 23, a plurality of comments on findings generated by the first generation unit 48 for two or more abnormal shadows in the group. In addition, in a case where designation of all abnormal shadows in the group is received by the first reception unit 52, the second display control unit 54 may perform control to display, on the display 23, a plurality of comments on findings generated by the first generation unit 48 for two or more abnormal shadows in the group.

Further, in a case where the designation of the abnormal shadow on the diagnosis target image is received by the first reception unit 52 and then an instruction to generate a comments on findings is received, the second display control unit 54 may perform control to display, on the display 23, the plurality of comments on findings generated by the first generation unit 48 for two or more abnormal shadows in the same group as the designated abnormal shadow. The instruction to generate the comment on findings in this case is received by the first reception unit 52, for example, in a case where the user presses a comment-on-findings generation button displayed on the display 23.

Figure 7:
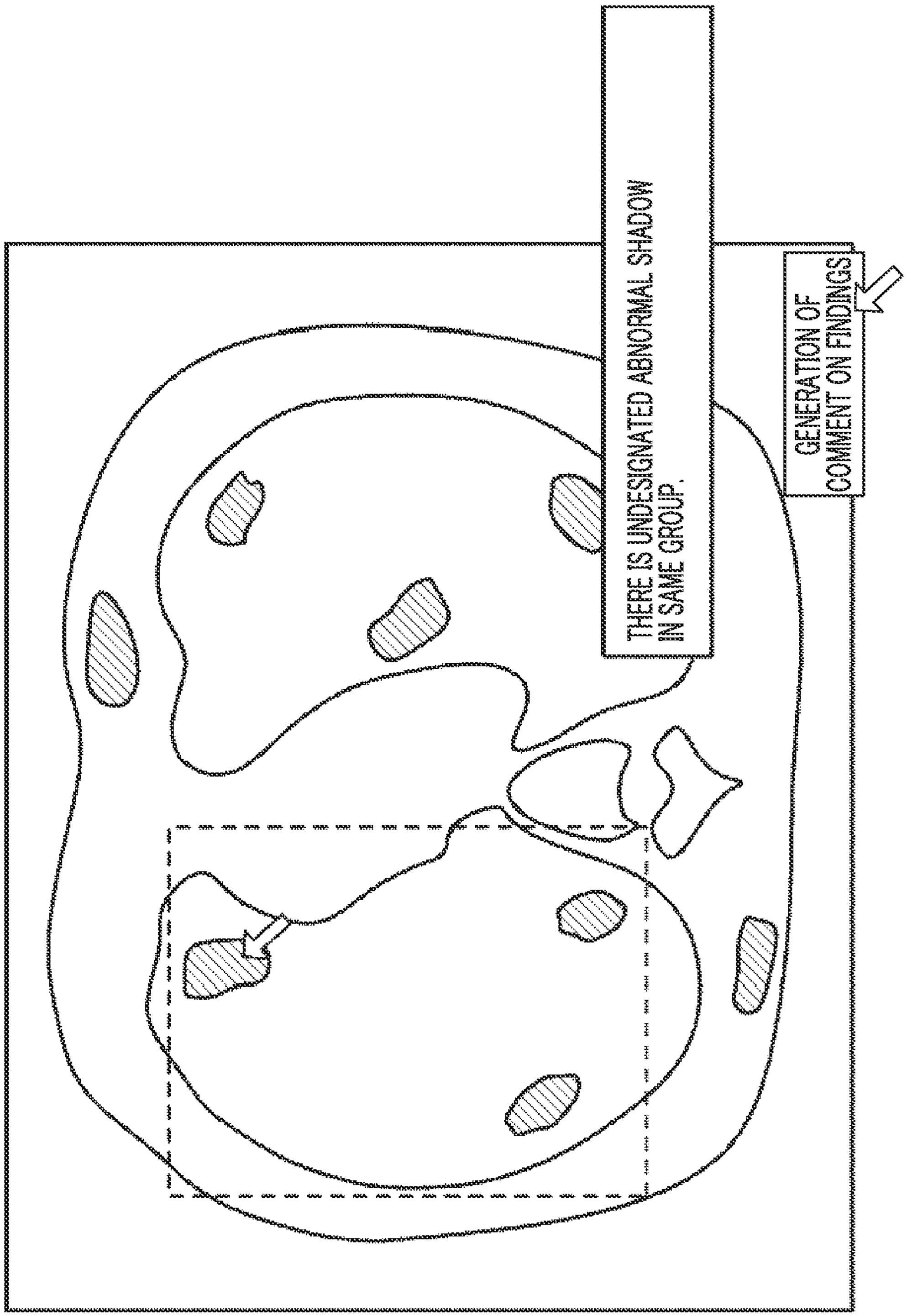
FIG. 7 is a diagram showing an example of a screen on which a notification that there are undesignated abnormal shadows is present.

Further, in a case where the instruction to generate the comment on findings is received by the first reception unit 52 and there is an undesignated abnormal shadow in the abnormal shadows in the same group as the designated abnormal shadow, the second display control unit 54 may notify that there is an undesignated abnormal shadow. Specifically, as shown in FIG. 7 as an example, the second display control unit 54 notifies that there is an undesignated abnormal shadow by performing control to display, on the display 23, a message to the effect that there is an undesignated abnormal shadow in the same group. FIG. 7 shows an example in which one abnormal shadow indicated by an arrow is designated from among three abnormal shadows in the same group surrounded by a broken-line rectangle and then the comment-on-findings generation button is pressed.

Figure 8:
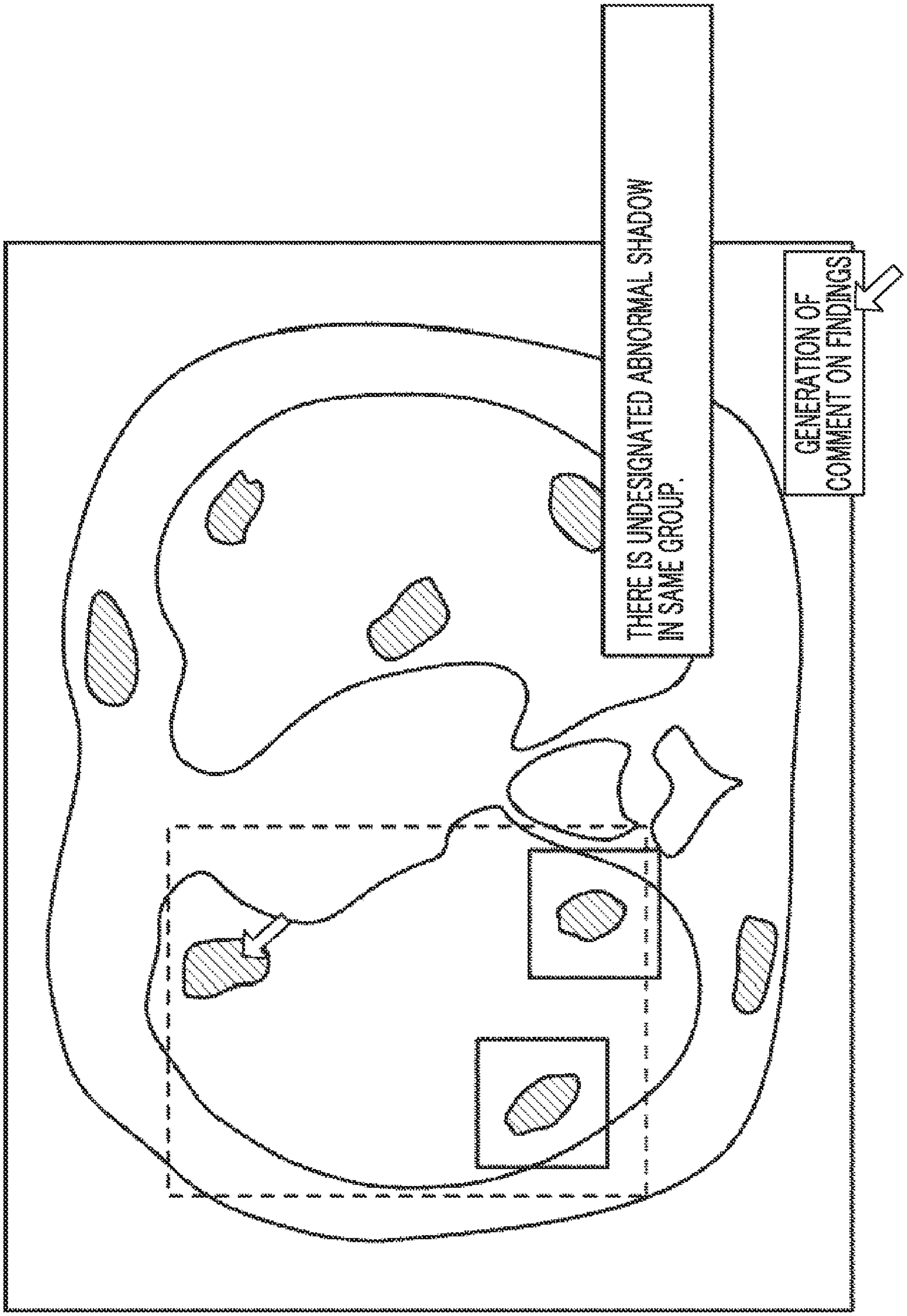
FIG. 8 is a diagram showing an example of a screen on which undesignated abnormal shadows are highlighted.

Further, in a case where the instruction to generate the comment on findings is received by the first reception unit 52 and there is an undesignated abnormal shadow in the abnormal shadows in the same group as the designated abnormal shadow, the second display control unit 54 may perform control to display information indicating the undesignated abnormal shadow. Specifically, as shown in FIG. 8 as an example, the second display control unit 54 performs control to highlight the undesignated abnormal shadow by surrounding the undesignated abnormal shadow with a solid-line rectangle. FIG. 8 shows an example in which one abnormal shadow indicated by an arrow is designated from among three abnormal shadows in the same group surrounded by a broken-line rectangle and then the comment-on-findings generation button is pressed.

The user selects one comment on findings to be described in the interpretation report from among the plurality of comments on findings displayed on the display 23. The second reception unit 56 receives the selection of one comment on findings from among the plurality of comments on findings by the user. The second generation unit 58 generates an interpretation report including the one comment on findings selected by the second reception unit 56.

The output unit 60 performs control to output the interpretation report generated by the second generation unit 58 to the storage unit 22 to store the interpretation report in the storage unit 22. Note that the output unit 60 may perform control to output the interpretation report generated by the second generation unit 58 on the display 23 to display the interpretation report on the display 23. The output unit 60 may also output the interpretation report generated by the second generation unit 58 to the interpretation report server 7 to transmit a request to register the interpretation report to the interpretation report server 7.

Figure 9:
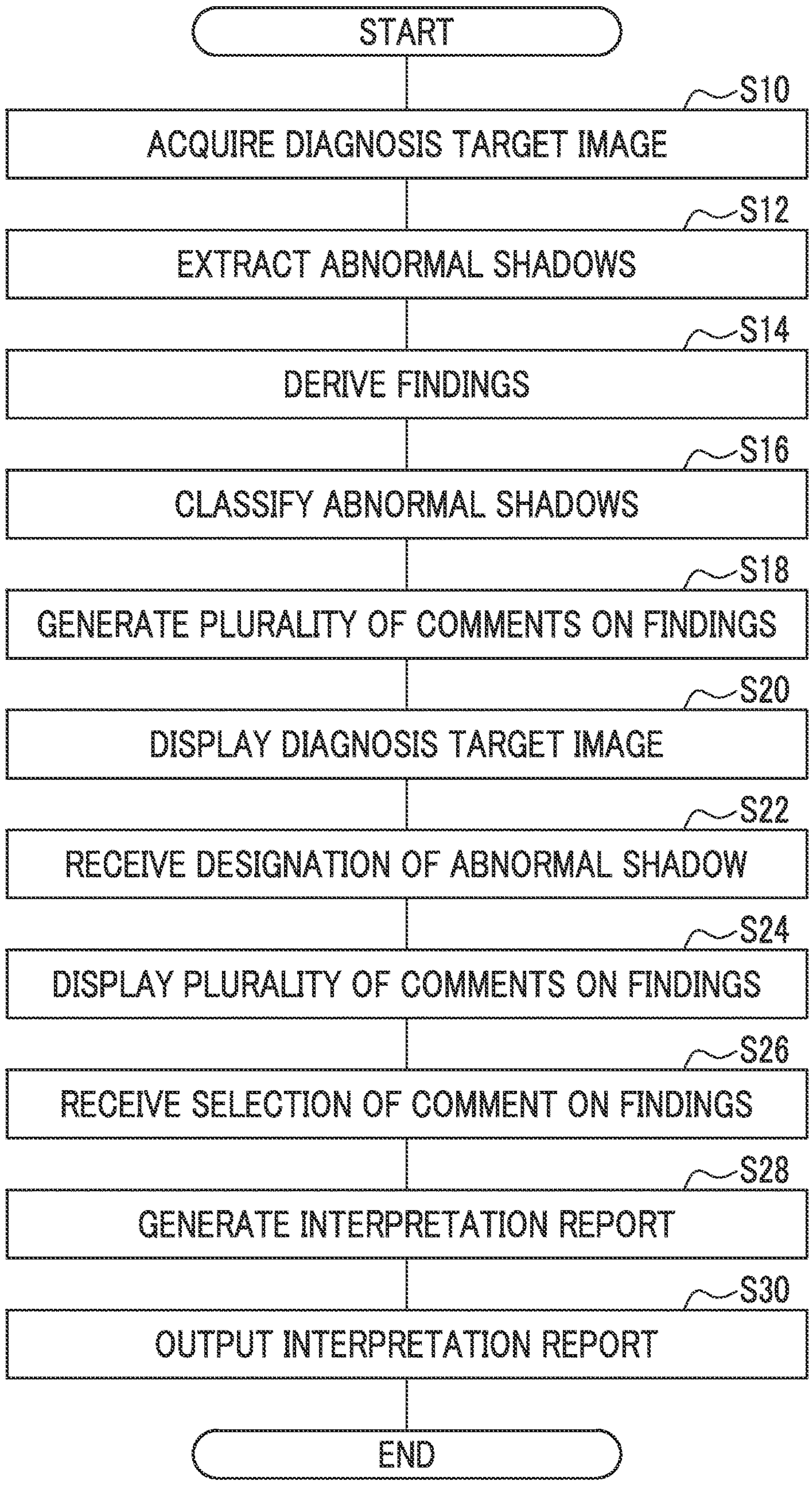
FIG. 9 is a flowchart showing an example of a document creation support process according to the first embodiment.

Next, with reference to FIG. 9, operations of the document creation support apparatus 10 according to the present embodiment will be described. The CPU 20 executes the document creation support program 30, whereby a document creation support process shown in FIG. 9 is executed. The document creation support process shown in FIG. 9 is executed, for example, in a case where an instruction to start execution is input by the user.

In Step S10 of FIG. 9, the acquisition unit 40 acquires the diagnosis target image from the image server 5 via the network OF 25. In Step S12, as described above, the extraction unit 42 extracts regions including abnormal shadows in the diagnosis target image acquired in Step S10 using the trained model M1. In Step S14, as described above, the analysis unit 44 analyzes each of the abnormal shadows extracted in Step S12 using the trained model M2, and derives findings of the abnormal shadows.

In Step S16, the classification unit 46 classifies a plurality of abnormal shadows extracted in Step S12 into at least one group based on the analysis result in Step S14, as described above. In Step S18, the first generation unit 48 generates a plurality of comments on findings for two or more abnormal shadows included in the same group, for each group in which the abnormal shadows are classified in Step S16, as described above.

In Step S20, the first display control unit 50 performs control to display the diagnosis target image acquired in Step S10 on the display 23. In Step S22, the first reception unit 52 receives the designation of one abnormal shadow by the user for the diagnosis target image displayed on the display 23 in Step S20. In Step S24, the second display control unit 54 performs control to display, on the display 23, a plurality of comments on findings generated in Step S18 for two or more abnormal shadows in the same group as the abnormal shadow whose designation is received in Step S22.

In Step S26, the second reception unit 56 receives the user's selection of one comment on findings from among the plurality of comments on findings displayed on the display 23 in Step S24. In Step S28, the second generation unit 58 generates an interpretation report including the one comment on findings selected in Step S26. In Step S30, the output unit 60 performs control to output the interpretation report generated in Step S28 to the storage unit 22 to store the interpretation report in the storage unit 22. In a case where the process of Step S30 ends, the document creation support process ends.

As described above, according to the present embodiment, it is possible to appropriately support the creation of the medical document even in a case where the medical image includes a plurality of regions of interest.

Second Embodiment

A second embodiment of the disclosed technology will be described. Since the configuration of the medical information system 1 and the hardware configuration of the document creation support apparatus 10 according to the present embodiment are the same as those of the first embodiment, the description thereof will be omitted.

In the first embodiment, a form example in which the document creation support apparatus 10 performs an analysis process on a diagnosis target image to classify a plurality of abnormal shadows into groups has been described. In the present embodiment, a form example in which the document creation support apparatus 10 classifies a plurality of abnormal shadows into groups based on the input from the user will be described.

Figure 10:
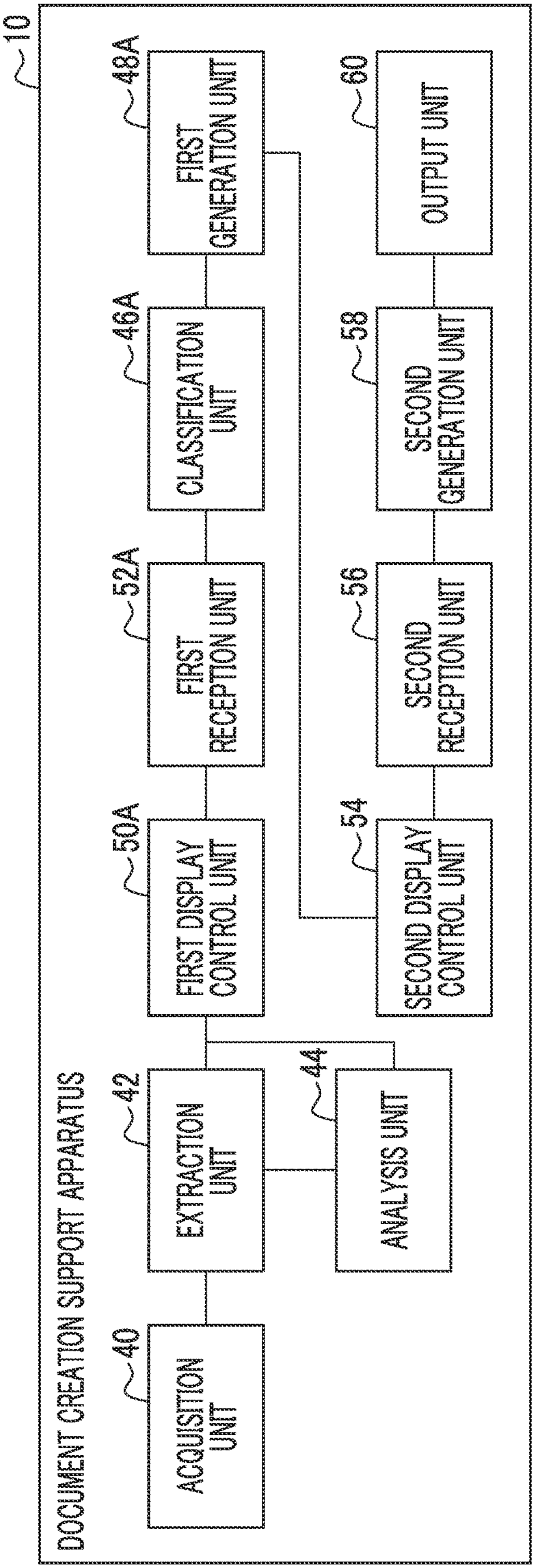
FIG. 10 is a block diagram showing an example of a functional configuration of a document creation support apparatus according to a second embodiment.

A functional configuration of the document creation support apparatus 10 according to the present embodiment will be described with reference to FIG. 10. The same reference numerals are assigned to the functional units having the same functions as the document creation support apparatus 10 according to the first embodiment, and the description thereof will be omitted. As shown in FIG. 10, the document creation support apparatus 10 includes an acquisition unit 40, an extraction unit 42, an analysis unit 44, a classification unit 46A, a first generation unit 48A, a first display control unit 50A, a first reception unit 52A, a second display control unit 54, a second reception unit 56, a second generation unit 58, and an output unit 60. The CPU 20 executes the document creation support program 30 to function as the acquisition unit 40, the extraction unit 42, the analysis unit 44, the classification unit 46A, the first generation unit 48A, the first display control unit 50A, the first reception unit 52A, the second display control unit 54, the second reception unit 56, the second generation unit 58, and the output unit 60.

The first display control unit 50A performs control to display a diagnosis target image on the display 23. At the time of this control, the first display control unit 50A may perform control to highlight the abnormal shadow extracted by the extraction unit 42. In this case, for example, the first display control unit 50A performs control to highlight the abnormal shadow by filling a region of the abnormal shadow with a color set in advance, surrounding the abnormal shadow with a rectangular frame line, or the like.

The user performs an operation of individually designating two or more abnormal shadows for which an interpretation report is to be created for the diagnosis target image displayed on the display 23. The first reception unit 52A receives designation of two or more abnormal shadows in the diagnosis target image by the user.

The classification unit 46A classifies two or more abnormal shadows into one group based on the input from the user. Specifically, the classification unit 46A classifies two or more abnormal shadows whose designation is received by the first reception unit 52A, that is, two or more abnormal shadows individually designated by the user, into one group.

The user may designate two or more abnormal shadows by range designation by a drag operation or the like of a mouse on the diagnosis target image. In this case, the classification unit 46A classifies two or more abnormal shadows included in the region designated by the user in the diagnosis target image into one group.

The first generation unit 48A generates a plurality of comments on findings only for two or more abnormal shadows included in one group classified by the classification unit 46A among the plurality of abnormal shadows extracted by the extraction unit 42. Since the process of generating a comment on findings is the same as the process of generating a comment on findings by the first generation unit 48 according to the first embodiment, the description thereof will be omitted.

Figure 11:
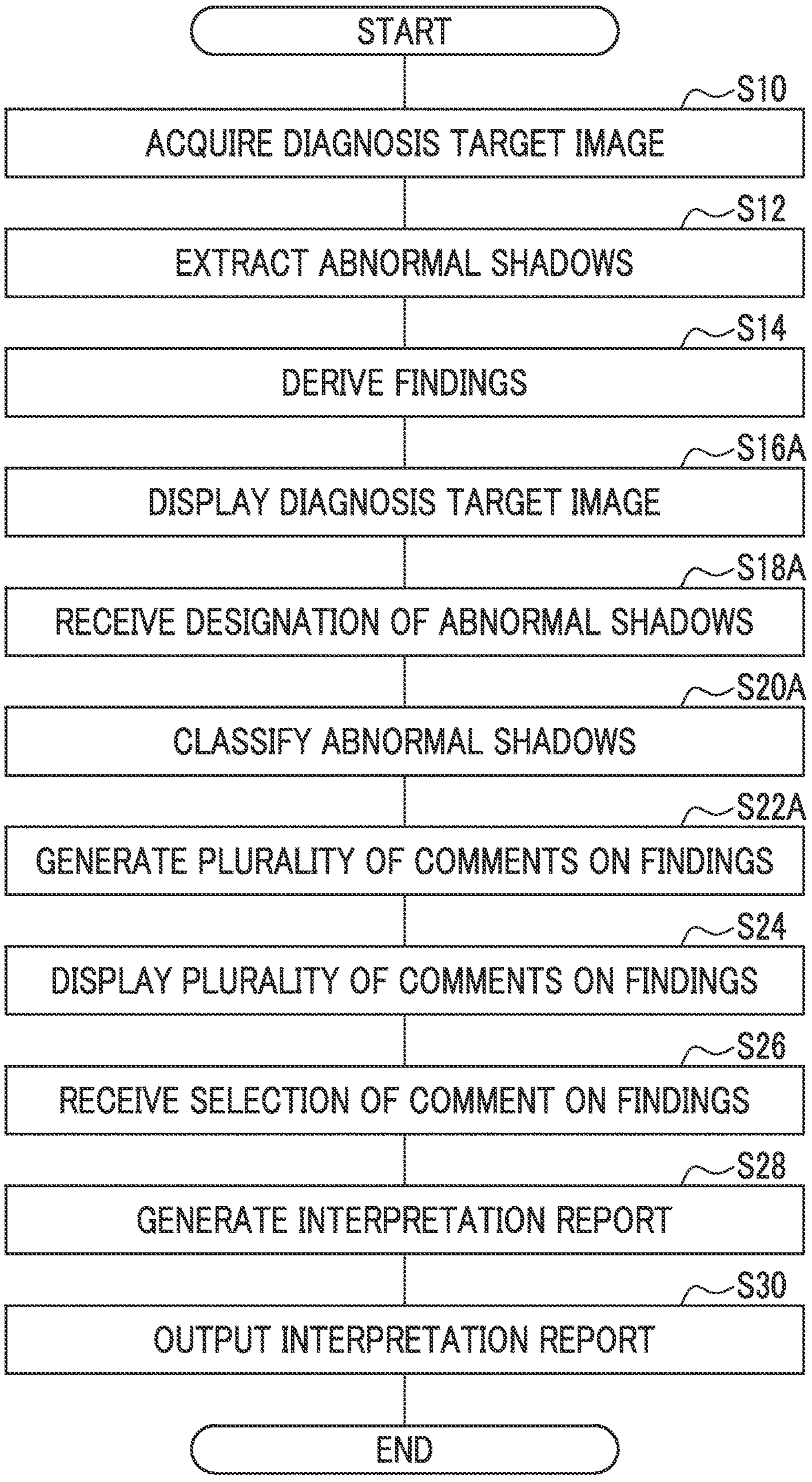
FIG. 11 is a flowchart showing an example of a document creation support process according to the second embodiment.

Next, with reference to FIG. 11, operations of the document creation support apparatus 10 according to the present embodiment will be described. The CPU 20 executes the document creation support program 30, whereby a document creation support process shown in FIG. 11 is executed. The document creation support process shown in FIG. 11 is executed, for example, in a case where an instruction to start execution is input by the user. Steps in FIG. 11 that execute the same processing as in FIG. 9 are given the same step numbers and descriptions thereof will be omitted.

In Step S16A of FIG. 11, the first display control unit 50A performs control to display the diagnosis target image acquired in Step S10 on the display 23. In Step S18A, the first reception unit 52A receives the designation of two or more abnormal shadows by the user for the diagnosis target image displayed on the display 23 in Step S16A.

In Step S20A, the classification unit 46A classifies two or more abnormal shadows whose designation is received in Step S18A into one group. In Step S22A, the first generation unit 48A generates a plurality of comments on findings only for two or more abnormal shadows included in one group classified in step S20A among the plurality of abnormal shadows extracted in Step S12. After Step S24, the same process as in the first embodiment is executed based on the plurality of comments on findings generated in Step S22A.

As described above, according to the present embodiment, the same effect as the first embodiment can be obtained.

In addition, in each of the above embodiments, the case where the region of the abnormal shadow is applied as the region of interest has been described, but the present disclosure is not limited thereto. As the region of interest, a region of an organ may be applied, or a region of an anatomical structure may be applied.

Further, in the first embodiment, in a case where two or more abnormal shadows belonging to different groups are designated by the user, that is, in a case where an instruction to generate a comment on findings is received by the first reception unit 52 and the two or more designated abnormal shadows belong to a plurality of different groups, the first generation unit 48 may generate a plurality of comments on findings as shown below. In this case, similarly to the first generation unit 48A according to the second embodiment, the first generation unit 48 may set two or more abnormal shadows designated by the user as one group and generate a plurality of comments on findings for the two or more abnormal shadows.

Further, in the second embodiment, the document creation support apparatus 10 may further include the classification unit 46 according to the first embodiment. In this case, in a case where the designation of the abnormal shadow on the diagnosis target image is received by the first reception unit 52A and there is an undesignated abnormal shadow in the abnormal shadows in the same group as the designated abnormal shadow, the first display control unit 50A may perform control to display, on the display 23, information recommending designation of the undesignated abnormal shadow. In this case, the two or more abnormal shadows designated by the user are classified into one group by the classification unit 46A based on the information.

Further, in this case, in a case where the designation of the abnormal shadow on the diagnosis target image is received by the first reception unit 52A and there is an undesignated abnormal shadow in the abnormal shadows in the same group as the designated abnormal shadow, the classification unit 46A may classify the undesignated abnormal shadow into the same group as the abnormal shadow designated by the user.

Moreover, in each of the above embodiments, the document creation support apparatus 10 may operate in the same manner as in the case where there are two or more regions of interest included in the group even in a case where there is one region of interest included in the group.

Further, in each of the above-described embodiments, for example, as a hardware structure of a processing unit that executes various kinds of processing, such as each functional unit of the document creation support apparatus 10, the following various processors can be used. As described above, the various processors include a programmable logic device (PLD) as a processor of which the circuit configuration can be changed after manufacture, such as a field programmable gate array (FPGA), a dedicated electrical circuit as a processor having a dedicated circuit configuration for executing specific processing such as an application specific integrated circuit (ASIC), and the like, in addition to the CPU as a general-purpose processor that functions as various processing units by executing software (programs).

One processing unit may be configured by one of the various processors, or may be configured by a combination of the same or different kinds of two or more processors (for example, a combination of a plurality of FPGAs or a combination of the CPU and the FPGA). In addition, a plurality of processing units may be configured by one processor.

As an example in which a plurality of processing units are configured by one processor, first, there is a form in which one processor is configured by a combination of one or more CPUs and software as typified by a computer, such as a client or a server, and this processor functions as a plurality of processing units. Second, there is a form in which a processor for realizing the function of the entire system including a plurality of processing units via one integrated circuit (IC) chip as typified by a system on chip (SoC) or the like is used. In this way, various processing units are configured by one or more of the above-described various processors as hardware structures.

Furthermore, as the hardware structure of the various processors, more specifically, an electrical circuit (circuitry) in which circuit elements such as semiconductor elements are combined can be used.

In each of the above embodiments, the document creation support program 30 has been described as being stored (installed) in the storage unit 22 in advance; however, the present disclosure is not limited thereto. The document creation support program 30 may be provided in a form recorded in a recording medium such as a compact disc read only memory (CD-ROM), a digital versatile disc read only memory (DVD-ROM), and a universal serial bus (USB) memory. In addition, the document creation support program 30 may be configured to be downloaded from an external device via a network.

The disclosures of Japanese Patent Application No. 2021-077650 filed on Apr. 30, 2021 and Japanese Patent Application No. 2021-208521 filed on Dec. 22, 2021 are incorporated herein by reference in their entirety. In addition, all literatures, patent applications, and technical standards described herein are incorporated by reference to the same extent as if the individual literature, patent applications, and technical standards were specifically and individually stated to be incorporated by reference.

What is claimed is:

1. A document creation support apparatus comprising at least one processor, wherein the processor is configured to:

acquire a medical image and information indicating a plurality of regions of interest included in the medical image;

classify two or more regions of interest among the plurality of regions of interest into a same group through an analysis process on the medical image;

generate a plurality of comments on findings for the two or more regions of interest in the same group;

perform control to display the medical image after generating the plurality of comments on findings;

receive designation of a region of interest on the medical image;

perform control to display the plurality of comments on findings for the two or more regions of interest in the same group as the designated region of interest;

receive selection of one comment on findings from among the plurality of comments on findings for the two or more regions of interest in the same group; and generate a medical document including the one comment on findings in the same group.

2. The document creation support apparatus according to claim 1, wherein the processor is configured to classify two or more regions of interest into the same group based on a degree of similarity of a region-of-interest portion included in the medical image.

3. The document creation support apparatus according to claim 1, wherein the processor is configured to classify two or more regions of interest into the same group based on a degree of similarity of a feature amount extracted from a region-of-interest portion included in the medical image.

4. The document creation support apparatus according to claim 1, wherein the processor is configured to classify two or more regions of interest having the same disease name derived from the region of interest into the same group.

5. The document creation support apparatus according to claim 1, wherein the processor is configured to:

generate a comment on findings for each of the plurality of regions of interest; and classify two or more regions of interest into the same group based on a degree of similarity of the generated comment on findings.

6. The document creation support apparatus according to claim 1, wherein the processor is configured to classify two or more regions of interest of which a distance between the regions of interest is less than a threshold value into the same group.

7. The document creation support apparatus according to claim 1, wherein the processor is configured to classify the plurality of regions of interest into at least one group based on anatomical relevance of the regions of interest.

8. The document creation support apparatus according to claim 1, wherein the processor is configured to classify the plurality of regions of interest into at least one group based on relevance of disease features of the regions of interest.

9. The document creation support apparatus according to claim 1, wherein the processor is further configured to, in a case where designation of at least one region of interest in a group is received, perform control to display the plurality of comments on findings for two or more regions of interest of the group.

10. The document creation support apparatus according to claim 9, wherein the processor is configured to, in a case where designation of a majority of regions of interest in the group is received, perform control to display the plurality of comments on findings for the two or more regions of interest of the group.

11. The document creation support apparatus according to claim 10, wherein the processor is configured to, in a case where designation of all regions of interest in the group is received, perform control to display the plurality of comments on findings for the two or more regions of interest of the group.

12. The document creation support apparatus according to claim 1, wherein the processor is configured to, in a case where the designation of the region of interest on the medical image is received and then an instruction to generate a comment on findings is received, perform control to display the plurality of comments on findings for the two or more regions of interest in the same group as the designated region of interest.

13. The document creation support apparatus according to claim 12, wherein the processor is configured to, in a case where the instruction to generate the comment on findings is received and there is an undesignated region of interest in the regions of interest in the same group as the designated region of interest, notify that there is an undesignated region of interest.

14. The document creation support apparatus according to claim 13, wherein the processor is configured to, in a case where the instruction to generate the comment on findings is received and there is an undesignated region of interest in the regions of interest in the same group as the designated region of interest, perform control to display information indicating the undesignated region of interest.

15. The document creation support apparatus according to claim 12, wherein the processor is configured to, in a case where the instruction to generate the comment on findings is received and two or more designated regions of interest belong to a plurality of different groups, generate a plurality of comments on findings for the two or more designated regions of interest.

16. The document creation support apparatus according to claim 1, wherein the processor is configured to:

in a case where designation of a region of interest on the medical image is received and there is an undesignated region of interest in the regions of interest in the same group as the designated region of interest, perform control to display information recommending designation of the undesignated region of interest.

17. The document creation support apparatus according to claim 1, in a case where designation of a region of interest on the medical image is received and there is an undesignated region of interest in the regions of interest in the same group as the designated region of interest, classify the undesignated region of interest into the same group as the region of interest designated by the user.

18. A document creation support method executed by a processor provided in a document creation support apparatus, the method comprising:

acquiring a medical image and information indicating a plurality of regions of interest included in the medical image;

classifying two or more regions of interest among the plurality of regions of interest into a same group through an analysis process on the medical image;

generating a plurality of comments on findings for the two or more regions of interest in the same group;

performing control to display the medical image after generating the plurality of comments on findings;

receiving designation of a region of interest on the medical image;

performing control to display the plurality of comments on findings for the two or more regions of interest in the same group as the designated region of interest;

receiving selection of one comment on findings from among the plurality of comments on findings for the two or more regions of interest in the same group; and generating a medical document including the one comment on findings in the same group.

19. A non-transitory computer-readable storage medium storing a document creation support program for causing a processor provided in a document creation support apparatus to execute:

acquiring a medical image and information indicating a plurality of regions of interest included in the medical image;

classifying two or more regions of interest among the plurality of regions of interest into a same group through an analysis process on the medical image;

generating a plurality of comments on findings for the two or more regions of interest in the same group;

performing control to display the medical image after generating the plurality of comments on findings;
receiving designation of a region of interest on the medical image;
performing control to display the plurality of comments on findings for the two or more regions of interest in the same group as the designated region of interest;
receiving selection of one comment on findings from among the plurality of comments on findings for the two or more regions of interest in the same group; and
generating a medical document including the one comment on findings in the same group.

* * * * *